United States Patent [19]
Everett, Jr. et al.

[11] Patent Number: 4,784,642
[45] Date of Patent: Nov. 15, 1988

[54] METERLESS DRAINAGE DEVICE WITH SUCTION CONTROL

[75] Inventors: Frederick A. Everett, Jr., Bloomfield; Quinton J. Farrar, Wyckoff, both of N.J.

[73] Assignee: Pfizer Hospital Products Group, Inc., New York, N.Y.

[21] Appl. No.: 916,342

[22] Filed: Oct. 7, 1986

[51] Int. Cl.[4] .......................................... A61M 1/00
[52] U.S. Cl. .................... 604/118; 604/318; 604/320; 137/205
[58] Field of Search ............... 137/205; 604/318–321, 604/118, 119

[56] References Cited

U.S. PATENT DOCUMENTS

| | | | |
|---|---|---|---|
| Re. 29,877 | 1/1979 | Kurtz et al. | 128/275 |
| 3,363,626 | 1/1968 | Bidwell et al. | 604/321 |
| 3,559,647 | 2/1971 | Bidwell et al. | 128/276 |
| 3,636,627 | 1/1968 | Bidwell et al. | 128/276 |
| 3,683,913 | 8/1972 | Kurtz et al. | 128/276 |
| 3,782,497 | 1/1974 | Bidwell et al. | 181/33 |
| 4,018,224 | 4/1977 | Kurtz et al. | 604/321 |
| 4,258,824 | 3/1981 | Kurtz et al. | 181/233 |
| 4,372,336 | 2/1983 | Cornell et al. | 137/205 |
| 4,425,125 | 1/1984 | Kurtz et al. | 604/321 |
| 4,519,796 | 9/1985 | Russo | 604/320 |
| 4,533,353 | 8/1985 | Akiyama | 604/321 |
| 4,534,765 | 8/1985 | Todd et al. | 604/321 |
| 4,540,413 | 9/1985 | Russo | 604/320 |
| 4,544,370 | 10/1985 | Elliott et al. | 604/319 |
| 4,675,011 | 6/1987 | Kurtz et al. | 604/320 |
| 4,698,060 | 10/1987 | D'Antonio et al. | 604/320 |
| 4,715,855 | 12/1987 | D'Antonio et al. | 604/320 |

FOREIGN PATENT DOCUMENTS

| | | | |
|---|---|---|---|
| 8403838 | 10/1984 | PCT Int'l Appl. | 604/321 |
| 86/01091 | 2/1986 | PCT Int'l Appl. | |
| 86/01114 | 2/1986 | PCT Int'l Appl. | |

OTHER PUBLICATIONS

Atrium Medical Corp., Amherst, N.H., 30331, 4 pages, 1983.
"Understanding Chest Drainage Systems—Deknatel Pleur-Evac ®", 1985.
"Airpot", Airpot Corp., Norwalk, Conn., 06851, 1982.

Primary Examiner—John D. Yasko
Assistant Examiner—J. L. Kruter
Attorney, Agent, or Firm—Pennie & Edmonds

[57] ABSTRACT

An apparatus for draining fluids, for example, from a chest or pleural cavity, includes a collection chamber for collecting fluids through an inlet port for entry of the fluids. Also included is a dry or waterless suction control chamber in fluid communication with the collection chamber for regulating the degree of vacuum imposed in the collection chamber. If desired, a seal chamber can also be provided between the dry suction control chamber and the collection chamber so as to prevent any ambient or atmospheric air from passing into the collection chamber. The suction control chamber has a first inlet which is coupled to a suction source and a second inlet communicates with the ambient. A waterless regulator is provided for regulating the degree of suction imposed in the collection chamber at a plurality of predetermined preset levels of suction. This regulator is positioned between the suction inlet and the ambient inlet. The suction control chamber also has at least a visual indicator disposed between the regulator and the suction inlet for providing immediate confirmation of proper operation of suction in the collection chamber.

The present invention also includes a device for retaining tubing under compression so as to provide self-sealing capability of the tubing during sampling or injection procedures.

34 Claims, 8 Drawing Sheets

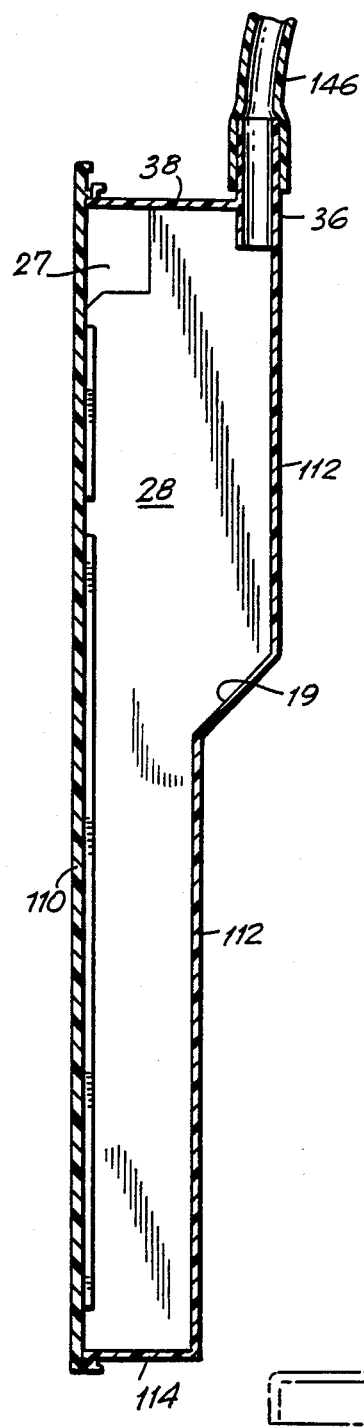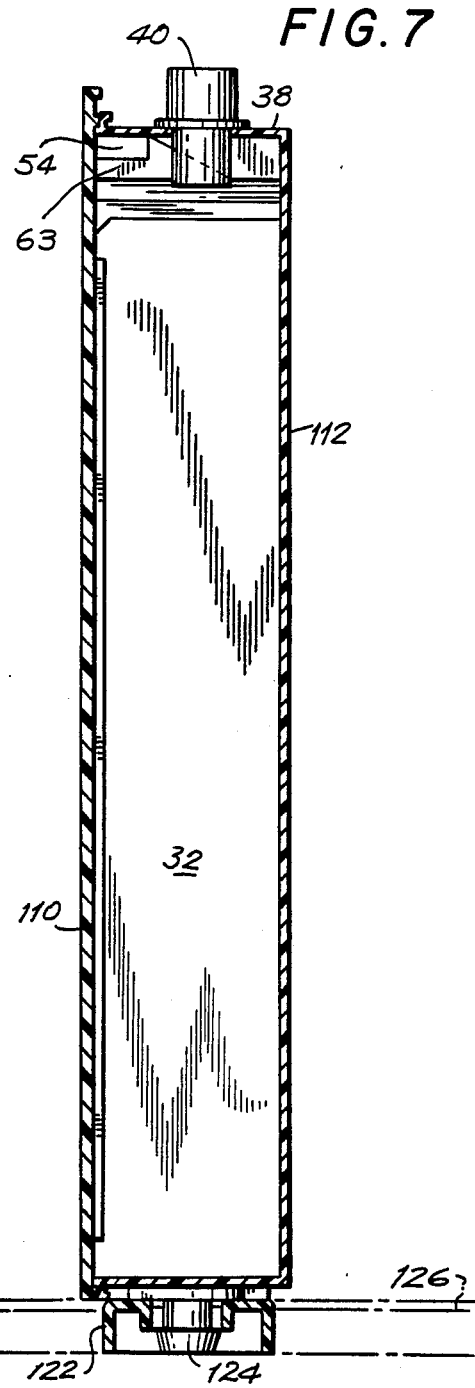

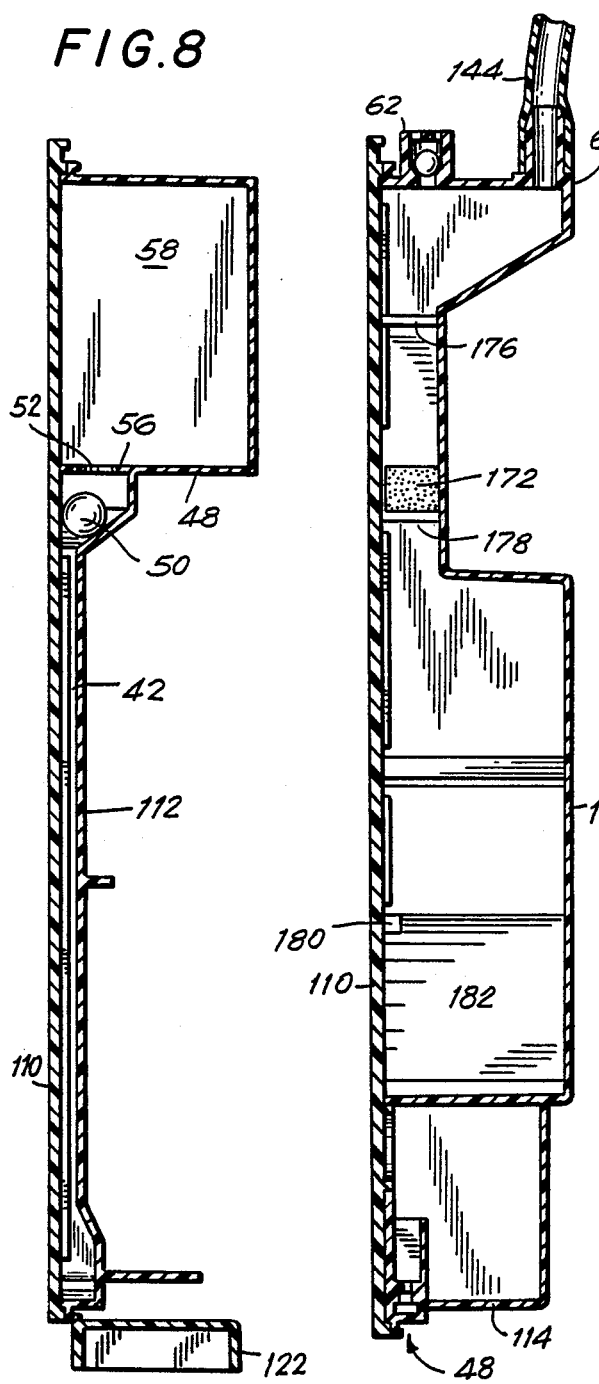
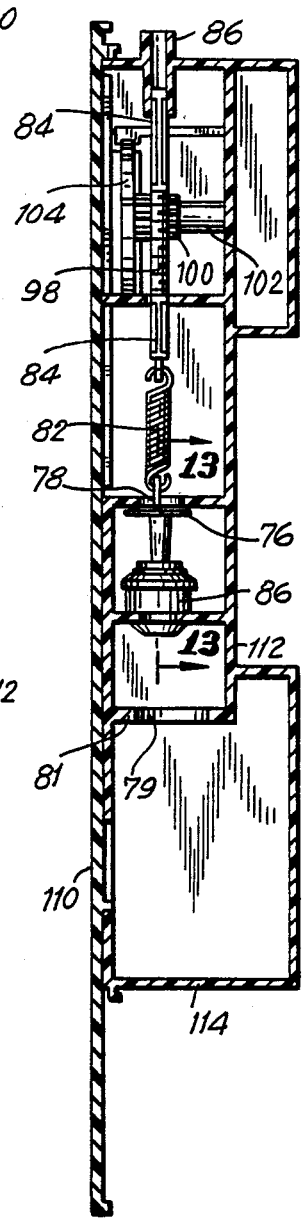
FIG.8    FIG.9    FIG.10

4,784,642

METERLESS DRAINAGE DEVICE WITH SUCTION CONTROL

TECHNICAL FIELD

The present invention relates to drainage devices and in particular to suction drainage systems for removal of gases or fluids from medical patients, such as from the chest cavity, by means of pressure differentials.

BACKGROUND ART

For many years, the standard apparatus for performing the evacuation of the pleural cavity was a drainage system known as the "3-bottle set-up" which includes a collection bottle, a water seal bottle and a suction control bottle. A catheter runs from the patient's pleural cavity to the collection bottle, and the suction bottle is connected by a tube to a suction source. The three bottles are connected in series by various tubes to apply suction to the pleural cavity to withdraw fluid and air and thereafter discharge the same into the collection bottle. Gases entering the collection bottle bubble through water in the water seal bottle. The water in the water seal also usually prevents the back flow of air into the chest cavity.

Suction pressure is usually provided by a central vacuum supply in a hospital so as to permit withdrawal of fluids such as blood, water and gas from a patient's pleural cavity by establishing a pressure differential between the suction source and the internal pressure in the patient. Such suction pressure and pressure differentials must be precisely maintained because of the dangerous conditions which could result if unduly high or low pressure differentials should occur. However, the hospital suction source typically can vary over time which degrades the suction performance. Also, drainage systems incorporating water filled manometers in the suction control chamber whose water level indicates fluid pressure are inconvenient because of the need to add water prior to use, as well as because of their size and weight. In addition, evaporation in the suction control chamber results in suction pressure variations which must be corrected by the addition of more water thereby increasing the maintenance and monitoring time required in the use of such drainage systems.

Also various inefficiencies have existed in the 3-bottle set-up resulting from the many separate components and the large number (usually 16 or 17) of connections, such as pneumothorax which may result from the loss of the water seal in the water seal bottle if suction were temporarily disconnected, and possible build-ups of positive pressure which could cause tension pneumothorax and possible mediastanal shift. Another serious shortcoming of the 3-bottle set-up is the possibility of incorrect connection and the time necessary to set the system up to monitor its operation.

The 3-bottle set-up lost favor with the introduction of an underwater seal drainage system sold under the name "Pleur-evac" ® in 1966 by Deknatel Inc.[1] U.S. Pat. Nos. 3,363,626; 3,363,627; 3,559,647; 3,683,913; 3,782,497; 4,258,824; and Re. 29,877 are directed to various aspects of the Pleur-evac ® system which over the years has provided improvements that eliminated various shortcomings of the 3-bottle set-up. These improvements have included the elimination of variations in the 3-bottle set-up that existed between different manufacturers, hospitals and hospital laboratories. Such variations include bottle size, tube length and diameter, stopper material and the like.

[1] A more detailed description of the need for and the proper use of chest drainage devices is presented in the Deknatel Inc. Pleur-evac ® publication entitled "Physiology of the Chest and Thoracic Catheters; Chest Drainage Systems No. 1 of a series from Deknatel" (1985) which is incorporated herein in its entirety.

Among the features of the Pleur-evac ® system which provide its improved performance are employment of 3-bottle techniques in a single, pre-formed, self-contained unit. The desired values of suction are generally established by the levels of water in the suction control bottle and the water seal bottle. These levels are filled according to specified values prior to the application of the system to the patient. A special valve referred to as the "High Negativity Valve" is included which is employed when the patient's negativity becomes sufficient to threaten loss of the water seal. Also, a "Positive Pressure Release Valve" in the large arm of the water seal chamber works to prevent a tension pneumothorax when pressure in the large arm of the water seal exceeds a prescribed value because of suction malfunction, accidental clamping or occlusion of the suction tube. The Pleur-evac ® system is disposable and helps in the battle to control cross-contamination.

Despite the advantages of the Pleur-evac ® system over the 3-bottle set-up and the general acceptance of the device in the medical community, there remains a continuing need to improve the convenience and performance of chest drainage systems and to render such systems compact. As noted above, fluid filled suction control chambers require the filling of manometer tubes to levels specified by the physician prior to being connected to the patient and the hospital suction system. Although it is conceivable that such filling could be performed at a manufacturing facility prior to shipment, as a practical matter this is undesirable because frequent adjustments may be needed according to the different values of patient suction as dictated by the attending physician. Moreover, the presence of fluid in the various tubes could result in damage to the system during shipment due to freezing temperatures or because of leakage. Furthermore, the levels of suction obtained by a chest drainage system are somewhat limited by the size of the manometer tubes required to maintain such suction levels. For high levels of suction, the size of manometers required would in some circumstances render the drainage system impractical. A reduction in size of the system would offer such benefits as ease of use, ease of storage, less expensive shipping costs, and the reduction in the obstruction between the patient, and visitors and the medical staff. In addition, accuracy of present underwater drainage systems is limited in that the various manometers employed must be constantly monitored visually by observing the liquid level in the respective chambers. Even when gauges are used, they likewise must be constantly monitored. In either case, when the fluid in the manometers evaporates, suction variations occur which require the addition of more water to compensate for the loss. All such activity of course is time consuming.

We have invented an improved drainage device which provides additional improvements to presently available devices.

SUMMARY OF THE INVENTION

The present invention is directed to an apparatus for draining fluids comprising a collection chamber for collecting fluids including an inlet for entry of the fluids; suction control chamber in fluid communication with the collection chamber for regulating the degree of vacuum imposed in the collection chamber and including first inlet for coupling to a suction source; second inlet communicating with the ambient; waterless means for regulating the degree of suction imposed in the collection chamber at a plurality of predetermined preset levels of suction, the regulating means disposed between the suction inlet and the ambient inlet; and indicator means disposed between the regulating means and the suction inlet for providing immediate confirmation of proper operation of suction in the collection chamber.

The regulation suction means comprises a member having an aperture and being disposed within and separating the suction control chamber into a first portion adjacent the ambient inlet and a remaining second portion adjacent the suction inlet and in fluid communication with the collection chamber; valve means dimensioned and configured for sealing the aperture; and means for tensioning the valve means closed when the collection chamber suction is at the preset level of suction and otherwise opening the valve means so as to permit ambient to flow into the second portion and thereby return the suction in the collection chamber to the preset level.

Preferably, the tensioning means comprises a spring under tension and coupled at one end to the valve means and at its other end to a support member within the first portion, so as to maintain the valve means in a closed sealing relationship with the aperture in accordance with the predetermined preset level of suction.

Also provided is means for adjusting the spring tension in predetermined preset discrete steps so as to provide one of the predetermined preset levels of suction. Preferably, the adjusting means comprises a worm gear disposed on at least a portion of the support member; pinion gear being rotatably supported and cooperatively engaging the worm gear; dial coupled to the pinion gear and having a plurality of predetermined preset grooves along its periphery; detent member resiliently disposed against the periphery and configured and dimensioned for seating within one of the grooves and such that upon rotating the dial, the detent member rides along said periphery until seating within one of the next grooves.

The apparatus of the present invention further comprises means for variably calibrating the tension of the spring while the detent member is seated within one of the predetermined preset grooves of the dial so that the spring tension can be selectively varied without any rotation of the dial. In one preferred embodiment, the tension calibration means comprises a collar rotatably disposed in a wall portion of the suction control chamber, the other end of the support member being secured to the collar for rotation therewith so that upon rotation of the collar together with the support member, the tension of the spring can be selectively varied while the dial is stationary. At least a portion of the dial extends out of the ambient inlet so that the dial can be rotated from outside of the suction control chamber. The dial has graduations thereon to indicate the suction pressure imposed in the collection chamber while the detent member is seated in one of the grooves.

Preferably, the valve means is a generally flat plate having a circular bead on one side thereof for seating against the separation member and about the aperture so as to provide in cross section a generally single point of contact between the bead and the separation plate. Also, the aperture in area is greater than the smallest cross-sectional area of any passage in any of the chambers.

The apparatus further comprises damping means coupled to the valve means for attenuating any rapid movement of the valve means during opening and closing of the aperture in response to any suction variations from the predetermined preset level of suction. The damping means comprises a dashpot operatively connected to the valve means. Also, the spring is disposed in said first portion adjacent the ambient inlet while the valve means and the dashpot are each disposed in the second portion.

In one preferred embodiment, the indicator means comprises a float disposed within a confined region of the second portion of the suction chamber, the confined region having a visible portion and the float being configured and dimensioned so as to move to the visible portion within the confined portion when the predetermined preset level of suction is obtained in the collection chamber and thereby provide immediate visual confirmation of proper operation of suction in the collection chamber. The confined region is defined between a pair of stop members and which limit the movement of the float within the confined region. Preferably the float is colored in contrast to its surroundings so as to be readily visible. The apparatus float can be flourescent so as to provide immediate visual confirmation of proper suction operation in reduced light or night conditions.

In an alternative embodiment, the indicator means comprises a visible bubbler zone for retaining a predetermined amount of fluid in the second portion of the suction control chamber so that under operational conditions ambient entering through the bubbler zone will bubble therethrough toward the suction inlet and thus provide both immediate visual and audible confirmation of proper operation of suction in the collection chamber. The bubbler zone includes a passageway bypassing the fluid retention zone. The passageway is dimensioned and configured so that ambient will not bubble through fluid in the bubbler zone until the suction imposed in the collection chamber is at least above set predetermined preset level of suction.

In another alternative embodiment, the apparatus for draining fluids includes a seal chamber for preventing passage of atmospheric air into the collection chamber.

The present invention is also directed to a device for regulating the degree of vacuum imposed in a drainage system comprising a housing defining a chamber adapted for fluid communication with the drainage system; first inlet in the housing for coupling to a suction source; second inlet in the housing communicating with the ambient; waterless means for regulating the degree of suction at a plurality of predetermined preset levels of suction, the regulating means disposed between the suction inlet and the ambient inlet; and indicator means disposed between the regulating means and the suction inlet for providing immediate confirmation of proper operation of suction. The regulation suction means comprises a wall member having an aperture and being disposed within and separating the chamber into a first portion adjacent the ambient inlet and a remaining second portion adjacent the suction inlet, the second portion adapted for fluid communication with the drainage system; valve means dimensioned and configured for sealing the aperture; and means for tensioning the valve means to seal the aperture when the drainage system suction is at the preset level of suction and otherwise unsealing the valve means so as to permit ambient to flow into the second portion and thereby return the suction in the drainage system to the preset level.

The present invention also relates to an apparatus for draining bodily fluids comprising collection chamber for collecting fluids from a body cavity, the collection chamber including an inlet for fluid communication with the body cavity; suction control chamber for regulating the degree of vacuum imposed in the collection chamber; and seal chamber for preventing passage of ambient into the collection chamber and including a large arm compartment having a suction inlet at one end; a small arm compartment at one end having an opening communicating with the collection chamber and communicating at its other end with the other end of the large arm, the small arm compartment having means adjacent its one end for preventing ambient from passing into the collection chamber when the collection chamber has a relatively high level of negative pressure. The ambient prevention means comprises a first chamber formed adjacent the opening and being dimensioned and configured so as to contain the entire volume of a predetermined amount of sealing fluid disposed in the seal chamber at the juncture of the large arm and the small arm compartments. The apparatus further comprises a second chamber disposed so as to separate the first containment chamber from the opening into the collection chamber so that any sealing fluid passing from the first containment chamber will enter into said second separation chamber and thereafter return to the containment chamber instead of passing through the opening. The containment chamber is configured so that any sealing fluid passing into the containment chamber is diverted in a direction other than the direction of normal flow so that entering fluid will circulate in and be collected within the containment chamber.

The apparatus further comprises a wall member positioned within the small arm and separating the containment chamber from the remainder of the small arm, the wall member having an aperture; and valve means being dimensioned and configured for opening and substantially closing the aperture, the valve means being normally open and tending to substantially close the aperture in response to any fluid entering into the containment chamber from the juncture of the large arm and the small arm compartments. The valve means comprises a ball dimensioned and configured so as to be adapted for seating with and substantially closing the aperture. This aperture includes a notch so as to permit the sealing fluid to enter into the containment chamber when the ball valve seats upon and substantially closes the opening whereupon the sealing fluid is diverted within the containment chamber generally transverse to the direction of normal flow. The remaining portion of the small arm is constricted so as to retain the ball valve movably between the constriction and the aperture. This remaining portion of the small arm is smaller in cross sectional area than that of the containment chamber. In one preferred embodiment, the ambient prevention means comprises a one-way check valve disposed and oriented in the small arm compartment. The valve when open permits the passage of suction flow from the collection chamber into the suction inlet, but when closed prevents ambient from passing into the collection chamber. The one-way check valve is positioned adjacent the opening communicating the small arm compartment with the collection chamber.

Preferably, the apparatus further comprises an air flow meter disposed at the juncture of the other ends of the small arm and large arm. The air flow meter provides for measurement of the quantity of gases passing from the body cavity. The apparatus also comprises a check valve means disposed in the large arm compartment. The check valve means is normally closed and tends to open to permit ambient into the seal chamber in response to substantially increased pressure within the seal chamber. Also, the present invention is directed to a chest drainage device for draining fluids from a body cavity or portion comprising a housing; collection chamber formed within the housing for collecting fluids including an inlet for entry of the fluids and for fluid communication with the body cavity or portion; seal chamber formed within the housing for preventing passage of ambient into the collection chamber and including a large arm compartment having a suction inlet at one end for coupling to a suction source; a small arm compartment at one end having an opening communicating with the collection chamber and communicating at its other end with the other end of the large arm, the small arm compartment having means adjacent its one end for preventing ambient from passing into the collection chamber when the collection chamber has a relatively high level of negative pressure; suction control chamber formed within the housing and being in fluid communication with the collection chamber for regulating the degree of vacuum imposed in the collection chamber and pleural cavity and including a first inlet for coupling to the suction inlet of the seal chamber; second inlet communicating with the ambient; waterless means for regulating the degree of suction imposed in the collection chamber at a plurality of predetermined preset levels of suction, the regulating means disposed between the first inlet and the ambient inlet; and indicator means disposed between the regulating means and the first inlet for providing immediate confirmation of proper operation of suction in the collection chamber.

Preferably, the housing is formed of a front wall member and a back wall member sealed together along their peripheries by a plurality of side wall members. The front wall member includes an integrally formed handle and the suction inlet and collection chamber inlet are each disposed in a first side wall common to the seal chamber and the collection chamber. Also, the ambient inlet to the suction control chamber is disposed in a second side wall adjacent to the first side wall.

The apparatus further comprises an elongated support stand rotatably secured to a third side wall opposite the first side wall so that the support stand can be rotated from a stored position to a support position wherein the support stand is generally transverse to the third side wall so as to stably support the housing at a predetermined location. The support stand can be secured in the support position.

Preferably, at least portions of the housing are transparent to permit viewing of the operation or contents of underlying portions of each of the collection, seal and suction control chambers. Also, at least selected portions of the front wall member are marked with graduations so as to identify the volume of the contents thereof and with predetermined indicia to provide instructional information.

In addition, the present invention is directed to an apparatus for draining fluids from a body cavity or portion comprising a collection chamber for collecting fluids including an inlet for entry of the fluids; tubing coupled at one end to the collection chamber inlet, the other end adapted for insertion into the body cavity or portion; compression means configured and dimensioned for snugly retaining a portion of the tubing under compression so as to provide self sealing capability of the tubing portion, the compression means having a port so as to expose the tubing and to provide access to the interior of the tubing upon insertion of a hypodermic needle; and suction control chamber in fluid communication with the collection chamber for regulating the degree of vacuum imposed in the collection chamber and including first inlet for coupling to a suction source; second inlet communicating with the ambient; waterless means for regulating the degree of suction imposed in the collection chamber at a plurality of predetermined preset levels of suction, the regulating means disposed between the suction inlet and the ambient inlet; and indicator means disposed between the regulating means and the suction inlet for providing immediate confirmation of proper operation of suction in the collection chamber.

Preferably, the compression means is formed of two like structured, elongated curved plate members having flanges extending along respective corresponding edges. The plate members are secured to each other along the flanges and the plate member opposite the port is relatively rigid so as to protect against penetration of a hypodermic needle.

Preferably, the inner cross sectional diameter of the curved plate members is less than the cross sectional outer diameter of the tubing. According to one preferred embodiment, the inner cross sectional diameter of the curved plate members is about four-fifths of that of the outer diameter of the tubing.

BRIEF DESCRIPTION OF THE DRAWINGS

The present invention is described in greater detail hereinbelow, with reference to the drawings wherein:

FIG. 6 is a first cross-sectional side view in the collection chamber taken along the lines 6—6 of FIG. 4.

FIG. 7 is a second cross-sectional side view in the collection chamber taken along the lines 7—7 of FIG. 4.

FIG. 8 is a first cross-sectional side view of the small arm of the seal chamber taken along the lines 8—8 of FIG. 4.

FIG. 9 is a cross-sectional side view in one compartment of the suction control chamber taken along the lines 9—9 of FIG. 4.

FIG. 10 is a cross-sectional side view in the second compartment of the suction control chamber taken along the lines 10—10 of FIG. 4.

DESCRIPTION OF THE PREFERRED EMBODIMENTS

In the description which follows, any reference to either orientation or direction is intended primarily for the purpose of illustration and is not intended in any way as a limitation of the scope of the present invention.

Figure 1:
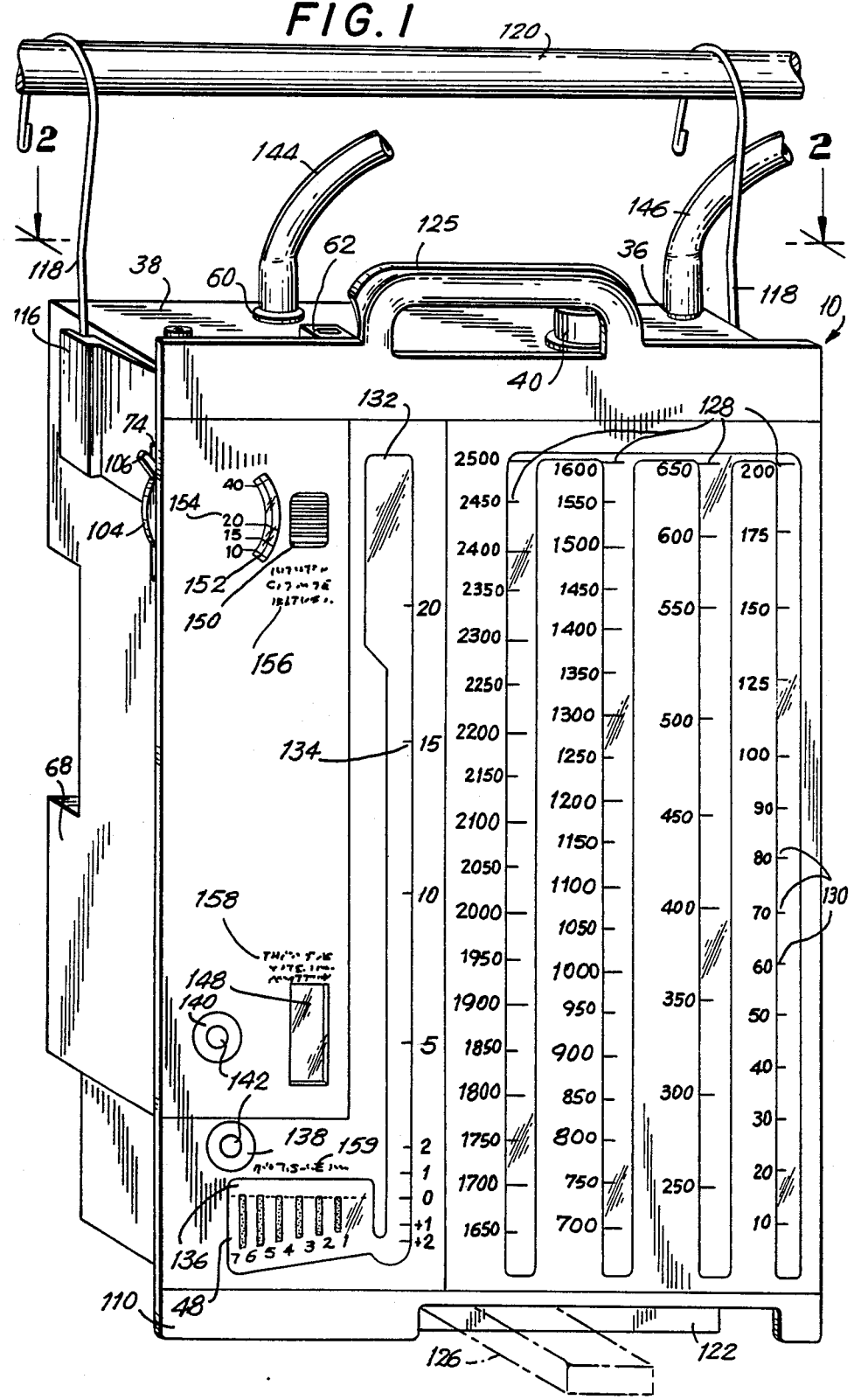
FIG. 1 is a perspective view of a chest drainage device according to the present invention supported in a hanging position.
Figure 4:
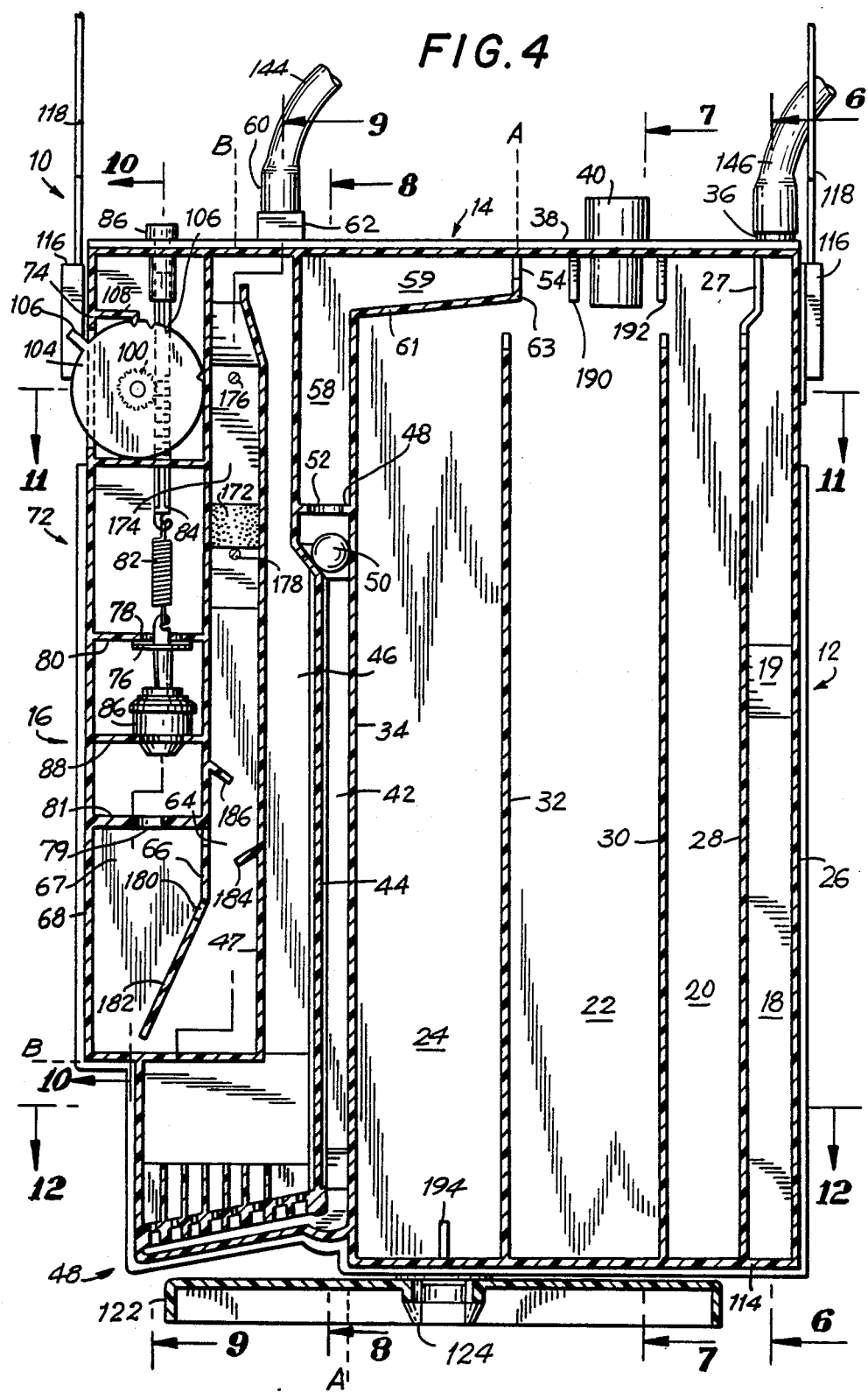
FIG. 4 is an exposed front view of the drainage device of FIG. 1.

Referring to FIG. 1 and 4, a chest drainage device 10 is illustrated with three chambers—a collection chamber 12 for retaining and storing fluids collected from a body cavity, a water seal chamber 14 for preventing any fluid from entering into the collection chamber 12 during high levels of negative pressure in the body cavity and a dry suction control chamber 16. The function and operation of these various chambers are generally described in U.S. Pat. Nos. 3,363,626; 3,363,627; 3,559,647; 3,683,913; 3,782,497; 4,258,824; and Re. 29,877 to the extent that like or common elements are presented therein. In addition, the purpose and general operation of the various chambers of the chest drainage device 10 of the present invention are also more fully described in the Deknatel Inc. Pleur-evac® publication entitled "Understanding Chest Drainage Systems" (1985). Accordingly, the disclosure of the aforementioned patents and publication are incorporated herein in their entirety.

The collection chamber 12 is formed generally to the right of line "A—A" and preferably includes four separate collection compartments 18, 20, 22 and 24 which are formed between respective pairs of walls 26, 28, 30, 32 and 34 as shown in FIG. 4. However, the collection chamber 12 of the present invention is not limited as to the number of separate collection compartments and any number as desired can be provided. Likewise, the volumetric size of the various collection compartments can be uniform or varied as preferred.

An inlet port 36 is positioned in top wall 38 so that fluid and gases from a body cavity pass directly into collection compartment 18. To provide for finer measurements of fluids collected, at least collection compartment 18 is dimensioned and configured to have the smallest volumetric size and the remaining compartments are preferably larger sized to accommodate greater amounts of fluid collected. In addition, sloping wall member 19 as shown more clearly in FIG. 6 permits the lower portion of compartment 18 to be smaller than the upper portion and thus provide yet even smaller volumetric measurements. An opening 27 in wall 28 as shown more clearly in FIG. 6 permits overflow of fluid from compartment 18 to pass first into compartment 20. Likewise, any overflow from compartment 20 can pass over upper edge of wall 30 into compartment 22 and from there over upper edge of wall 32 into compartment 24. Accordingly, the upper edges of walls 30 and 32 are approximately at the same height to allow for overflow.

A high negativity valve 40 is positioned in top wall 38 in communication with collection chamber 12. The high negativity valve includes a button actuated valve which when depressed allows filtered air to enter the collection chamber 12. In this manner, undesired high degrees of negative pressure that may occur in the body cavity and thereby develop in the collection chamber 12 are relieved.

The seal chamber 14 generally is formed between the lines "A—A" and "B—B" as shown in FIG. 4. In particular, the seal chamber 14 includes a small arm compartment 42 formed between walls 34 and 44 and a large compartment 46 formed between walls 44 and 47. Although seal chambers are typically operated with a predetermined level of fluid such as water, the seal chamber 14 of the present invention can be operated in either a "dry" or a "wet" mode of operation in the manner to be more fully described hereinbelow. An air flow meter 48, if desired, can be positioned as shown in FIGS. 1 and 4 at the juncture of the lower ends of the small and large arm compartments 42, 46. The air flow meter 48 is intended for use in the "wet" mode and is of the type illustrated and described in aforementioned U.S. Pat. No. 3,683,913 whose disclosure is incorporated herein in its entirety. However, even if operated in the "dry" mode, the air flow meter 48 if present will have no deleterious effect.

The seal chamber 14 preferably also includes a valve mechanism in the small arm compartment 42 which includes a plate member 48 and a ball float valve 50 that is free to travel between plate member 48 and a constricted portion of small arm compartment 42 as shown in FIG. 4. However, the constricted portion as shown more clearly in FIG. 8 is configured so that in operation under suction, the float ball valve 50 will not block off the lower portion of the small air compartment 42.

Plate member 48 as shown more clearly in FIG. 8 includes a circular opening 52 which is configured and dimensioned so as to permit ball float valve 50 to seat within opening 52 when fluid such as water which is typically contained within the water seal chamber 14 is drawn by unduly high negative pressure toward the collection chamber 12 through opening 54 in the upper end of the small arm compartment 42. A similar valve arrangement is also described as a cylindrical valve member in U.S. Pat. No. 3,683,913 which also serves to retain water or fluid in the water seal chamber. However, plate number 48 according to the present invention includes a notch or keyway slot 56 which still permits fluid or water from the water seal chamber to bypass ball valve 50 and enter into the upper end 58 of small arm compartment 42. Within the upper end compartment 58, the fluid bypasses ball valve 50 and circulates in a direction transverse to the flow of suction or normal flow and is diverted upon the walls forming upper end compartment 58.

Preferably, the upper end compartment 58 is configured and dimensioned so as to accommodate the entire fluid volume in the water seal chamber to be contained therein. In this manner, water in the water seal chamber is prevented from being drawn into the collection chamber through opening 54 in the event of a high negativity developed in the collection chamber 12. Such high negativity occurrences can result from a deep breath, coughing or choking by the patient. It can also occur when suction is turned off which happens either when the suction tube is occluded or the hospital suction fails. High negativity can likewise occur when the patient is on a ventilator. Alternatively high negativity results when medical personnel milk the tubing from the drainage device to the patient. In the latter case, milking is the process whereby clots in the tubing are pushed into the collection chamber 12 by grasping the tubing with one hand behind the clot and squeezing the tubing toward the collection chamber 12 so as to advance the clot thereto.

Although the small end compartment 42 is illustrated with a ball float valve 50 in the small arm compartment, the configuration of upper end compartment 58 is suitable to provide for prevention of any fluid from the water seal chamber 14 passing into the collection chamber 12. Thus the ball float valve 50 is but an additional safeguard which can be optionally incorporated and used with the structure of the upper end compartment 58. An additional chamber 59 separates the containment chamber or upper end compartment 58 from opening 54 so as to aid in preventing fluid from passing into the collection chamber 12. Preferably the separation chamber 59 has a sloping lower surface 61 as shown in FIG. 4 and opening 54 is positioned uppermost in wall 63.

Figure 8A:
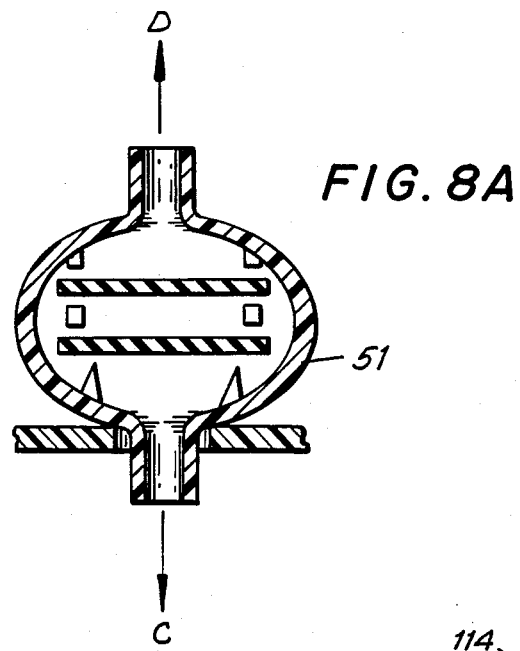
FIG. 8a is an enlarged cross-sectional side view of the small arm of the seal chamber taken along the lines 8—8 of FIG. 4 illustrating an alternative embodiment of a check valve for dry operation of the seal chamber.

In an alternative embodiment, the seal chamber 14 can be operated in a dry mode without any fluid required to maintain a seal. In such instance, the ball float valve 50 can be replaced with a check valve 51 which seats in compartment 58 and about opening 52 as shown in FIG. 8A. The check valve 51 is a one way valve that permits suction flow in the direction of arrow "C" but closes and prevents any flow of ambient or atmospheric air into collection chamber 12 in the direction of arrow "D."

The upper end of the large arm compartment 46 of the water seal chamber 14 is in fluid communication with suction inlet port 60 and a positive pressure relief valve 62 as shown in FIG. 4. Alternatively, this valve 62 can be positioned, if desired, in the large arm 46 of the seal chamber 14 or in the suction line itself. The valve 62 is of the check type configuration which is normally closed and includes valve member 63. it opens to permit excessive pressure in the seal chamber 14 to be vented to the ambient or atmosphere in response to any substantially increased pressure within the seal chamber 14.

Figure 5:
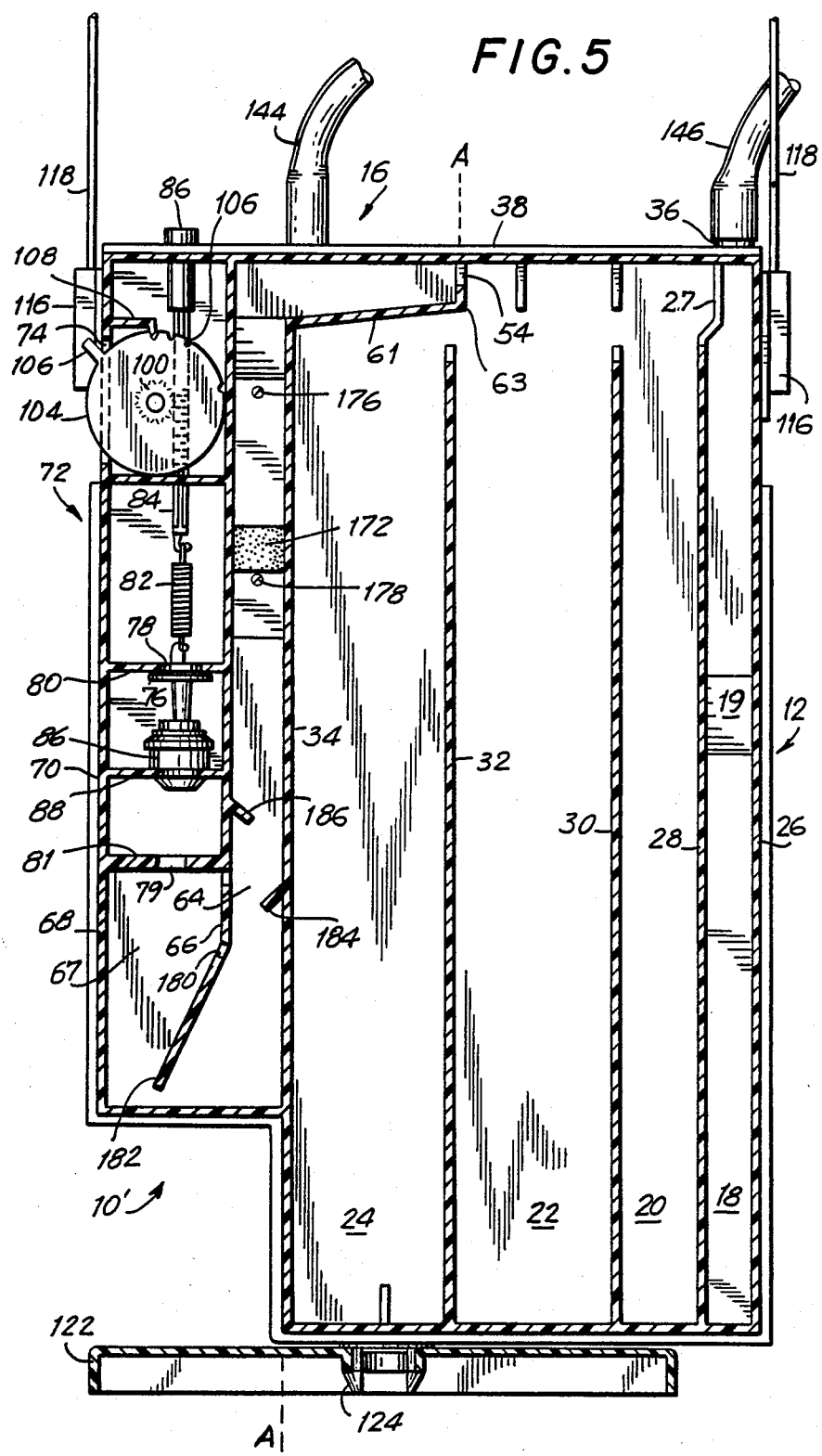
FIG. 5 is an exposed front view of an alternative embodiment of the drainage device of the present invention.
Figure 11:
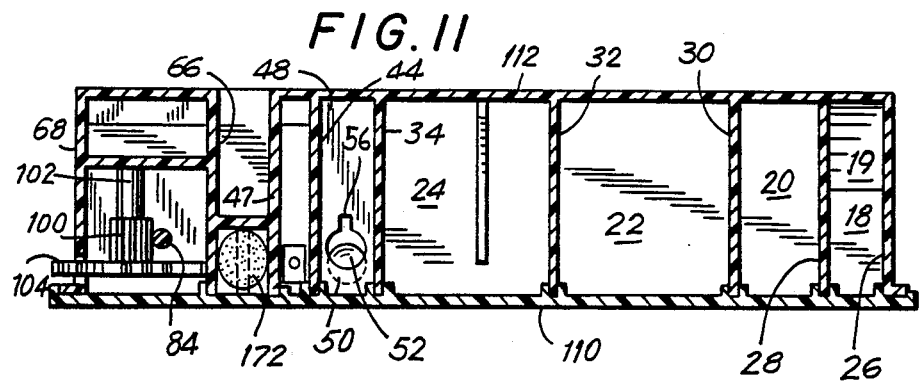
FIG. 11 is a cross-sectional view taken along lines 11—11 of FIG. 4.
Figure 12:
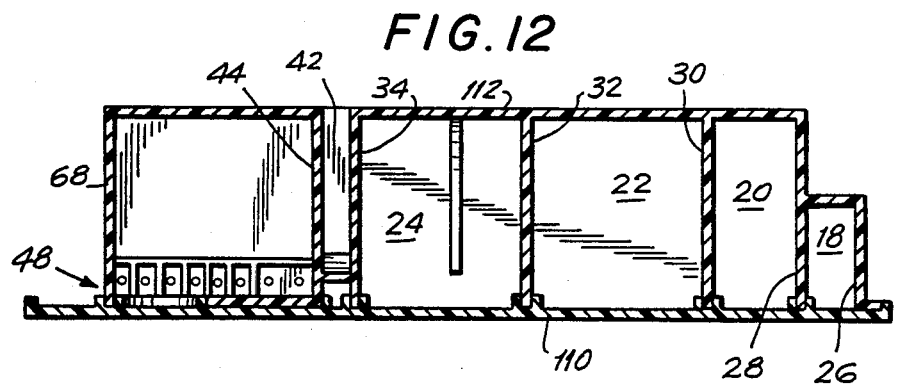
FIG. 12 is a cross-sectional view taken along lines 12—12 of FIG. 4.
Figure 13:
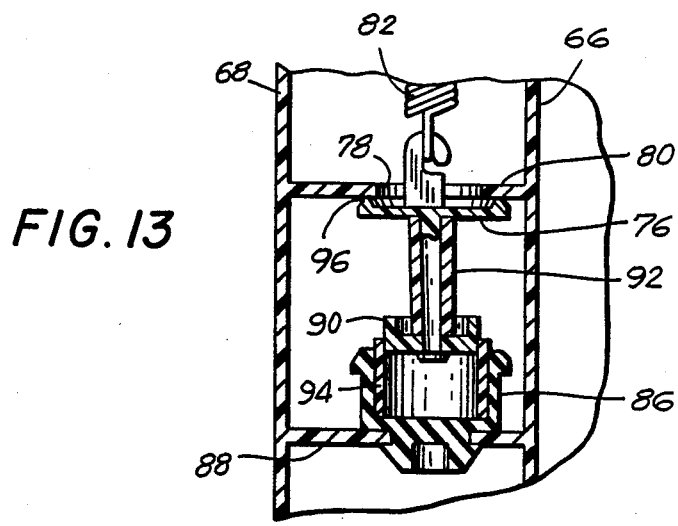
FIG. 13 is an enlarged view illustrating the poppet valve and dashpot in the suction control chamber taken along lines 13—13 of FIG. 10.

The chest drainage device 10 according to the present invention also includes a suction control chamber 16 which includes a first compartment 64 formed between walls 47 and 66 and a second compartment 67 formed between walls 66 and 68. The upper end of first compartment 64 is fluidly coupled to the suction inlet port 60 together with the upper end of the large arm 46 of the water seal chamber 14. The upper end of the second compartment 67 which is formed between walls 66 and 68 includes a waterless suction regulator 72 which is housed in the upper portion of second compartment 67 as shown in FIG. 4. The upper end of compartment 67 has an opening 74 which communicates with the atmosphere or the ambient about the chest drainage device 10. The suction regulator 72 includes a valve 76 which is configured and dimensioned to seat against opening 78 in a plate member 80 which separates the second compartment 67 as shown in FIG. 5 into an upper and a lower portion. As evident from the drawings, the plate valve 76 is positioned in the lower portion and is biased in a closed position by means of a coil spring 82 which is secured to the hook end of rod 84 and whose other end is secured in the upper wall 38 in a rotatable joint coupling or collar 86 which is annular in configuration. The other end of rod 84 is positioned within the hollow portion of annular collar 86. The collar 86 also has a keyway ridge that is received within a groove along the upper end of rod 84. In this fashion, the rod 84 can be rotated together with the collar 86 and simultaneously advanced upwardly or downwardly as will be described hereinbelow. The plate valve 76 as shown more clearly in FIG. 13 is formed on the end of a dashpot 86 which is secured in plate member 88 that is smaller sized than plate member 80 to permit atmospheric air to pass thereby. The dash pot 86 is of the type manufactured under the trademark Airpot which is manufactured by Airpot Corporation, 27 Lois Street, Norwalk, Connecticut. The dashpot 86 attenuates the rapid modulation of the valve 76 which may occur during the operation of the chest drainage device 10. Preferably the dashport 86 includes a graphite plug 90 attached to a stem 92 of plate valve 76. The graphite plug 90 rides within a well formed of a glass annulus 94 which together with the graphite plug 90 provide non binding surfaces to avoid sticking of component parts.

As shown more clearly in FIG. 13, the plate valve 76 is a generally flat plate with a circular bead 96 for seating against plate member 80 and about opening 78. In this manner, the plate valve 76 in cross section generally provides a single point of contact between the bead 96 and plate member 80. This eliminates large contacting surface areas and thereby prevents any sticking of the plate valve 76 that may occur due to moisture. Preferably the plate valve 76 is formed of a high density polyethylene which is more pliable than the plate member 80. In this fashion, the plate valve 76 will more easily conform to any irregularities in the plate member 80 and assure proper sealing of the opening 78.

The rod 84 includes as shown more clearly in FIG. 10 a portion having a worm gear 98 that cooperates with a gear 100 positioned on a shaft 102 that supports rotatably positioned disk 104 having lever arm 106. Accordingly, as gear 100 is rotated upon movement of lever 106, the worm gear 98 and rod 84 are advanced upwardly or downwardly while collar 86 remains fixed or non-rotating and thereby changes the tension of the spring 82 that provides the amount of force for seating valve plate 76 against opening 78. Such tension corresponds to the amount of suction imposed in the collection chamber 12 and likewise the patient's pleural cavity and can thereby be calibrated so as to provide for a plurality of predetermined, preset values that can thereby be marked on the disk 104. To provide for accurate positioning of the disk 104, a corresponding series of detents 106 are provided along prescribed portions of the circumference of disk 104 and cooperate with a stop arm 108 that seats at its outer end within any one of the predetermined preset detents 106 that correspond to a pre-set level of suction. The stop arm 108 is supported from outer wall 68 that includes opening 74 that permits ambient or atmosphere to enter the suction control chamber 16. As noted above, rotation of collar 86 simultaneously allows the rod 84 to be advanced upwardly or downwardly while the disk 104 is in a given position in order to provide for proper calibration of the suction level settings.

The suction control chamber 16 includes a visual indicator that provides immediate confirmation of proper operation of suction in the collection chamber 12. This visual indicator will be described in greater detail below.

Figure 2:
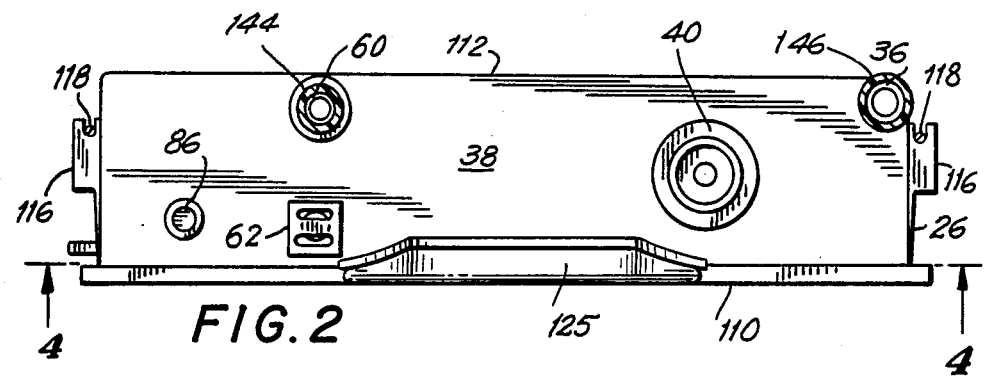
FIG. 2 is a top view of the drainage device of FIG. 1 illustrating the inlet ports into the collection chamber and the suction control chamber.
Figure 3:
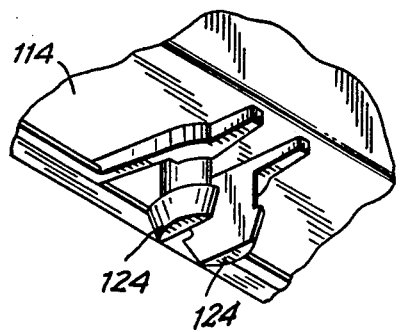
FIG. 3 is an enlarged view of a portion of the bottom of the drainage device of FIG. 1 before attachment of the floor stand.

As shown in FIG. 1, the drainage device 10 is generally formed of a housing that includes a front wall 110 that is secured to a back wall !12. The front wall 110 and the back wall 112 are joined by means of four side walls which includes a top wall 38 as shown more clearly in FIG. 2, right side wall 26 and left side wall 68 and a bottom wall 114. As shown in FIGS. 6 through 10, the different walls and sides can have different contours in order to accommodate the different chambers defined therebetween. In one preferred embodiment, the housing can be formed integrally with all the walls joined along their peripheries. Alternatively, the separate side walls and front and back walls can be secured to one another by suitable means which are well known to those skilled in the art. According to the preferred embodiment illustrated in FIG. 1, the housing 10 includes side brackets 116 shown more clearly in FIG. 2 from which hangers 118 extend in order to permit the device 10 to be supported from a support rod 120 such as a hospital bedpost or the like. In an alternative embodiment, the device 10 includes a floor support stand 122 which is secured rotatably to the bottom wall 114 as shown in FIG. 4. The floor stand 122 comprises a generally rectangular or elongated bar which has an aperture centrally positioned so as to be able to pass over the split collar 124 as shown in FIG. 3. In this manner the floor stand 122 once assembled over the split collar 124 is able to rotate about its opening and can be positioned in a support fashion transversely to the longitudal axis of bottom wall 114 as shown in phantom lines in FIGS. 1 and 7 indicated as element 126. If desired, the floor stand 122 can be secured after being placed in the support position. Also, the housing front wall 110 preferably includes an integrally formed handle 125 for ease in carrying and handling.

In order to permit viewing of the contents of the collection chambers, the front wall 110 as shown in FIG. 1 is at least transparent at certain portions 128 thereof which overlay the heights of the various collection compartments. Also, the heights are calibrated with graduations 130 which indicate the amount of fluid collected therein. As noted above, the smaller volumetric size of the first collection compartment permits finer measurements, for example, from 0-200 cc of fluid while the other compartments accommodate still larger volumetric amounts. In this manner, the medical personnel can readily evaluate the performance of the chest drainage device 10 as the amount of fluid collected over time and during a complete fluid evacuation procedure by a single reading of the height of the fluid in the most recently filled collection compartment.

Other portions of front wall 110 are also transparent to permit the viewing of additional operational features of the device 10. In this respect, the small arm compartment 42 of the sealed chamber 14 is transparent 132 in order to permit viewing of the height of the fluid contained within the seal chamber 14. Accordingly, the length of the small arm compartment 42 is also calibrated with graduations 134 in order to permit ready measurement of the height of the fluid. Similarly the airflow meter 48 has a transparent portion 136 which allows viewing of any air bubbles passing therethrough.

In order to allow for filling of the fluid into the seal chamber 14, a grommet 138 is provided as shown in FIG. 1. Similarly a grommet 140 is provided in front wall 110 so as to permit injection of fluid if desired into the juncture of the first and second compartments 64, 67 in the suction control chamber 16. These grommets 138 and 140 include a central rubber portion 142 which permits injection of fluid by means of a hypodermic needle which will penetrate but not damage the rubber seal that thereafter self-seals and retains the integrity of the respective chambers or portions thereof.

As shown in FIG. 1, the device 10 is coupled to a suction source by means of a suitable tubing 144 that is connected over the suction inlet 60. In a similar fashion a tubing 146 is employed for connection to the collection chamber inlet 36 and has its other end adapted for insertion into the body cavity or portion if desired so as to permit evacuation of gases and fluids therefrom.

Also, the suction control chamber 16 underlies a transparent portion 148 that permits viewing of the optional bubbling operation, if utilized as desired, in that chamber portion and thereby provides both a visual and audible confirmation of operation of suction. Similarly, a transparent portion 150 permits visual confirmation of operation in the first compartment 64 of the suction control chamber 16 in a manner to be described in greater detail below. In this manner, medical personnel can easily determine upon viewing through either portions 148 or 150 that the device 10 is properly operating. In order to permit visual determination of the proper level of suction setting desired, the disk 104 is viewable through transparent portion 152 which is calibrated with indicia 154 that indicate readily the degree of suction which is selected by means of movement of lever arm 106 extending through opening 74 of left side wall 68. Instructional information can be provided on the face of front wall 110 as shown at different locations 156, 158 and 159.

An alternative embodiment 10' of the chest drainage device 10 according to the present invention is illustrated in FIG. 5. For ease of convenience elements of chest drainage device 10' that are common to like elements in the embodiment 10 of FIG. 4 are identified by like numerals. However, the embodiment of the chest drainage device 10' of FIG. 5 has a collection chamber 12 which is in direct fluid communication with suction control chamber 16 through opening 54 in wall 63 without a seal chamber as shown in the embodiment depicted in FIG. 4. Acordingly, in FIG. 5, the collection chamber 12 is formed to the right of lines "A—A" and suction control chamber 16 to the left thereof.

During the drainage procedure, it is at times advantageous or desirable to draw a fresh sample of fluid drainage from the patient for culture purposes or other testing procedures. It is also advantageous or desirable to provide for introduction of antibiotics as well as other drugs back to the patient in the event infection is detected. According to currently available methods for obtaining drainage samples, some chest drainage devices include a resealable site in the collection chamber 12. However, with this method the clinician or medical personnel cannot obtain a fresh sample since the collection chamber 12 invariably would contain fluids that have collected over a period of time. Nor does such resealable site allow for the infusion of any drugs to the patient. Another common method is to sample directly through the patient tubing which is typically formed of latex. Although manufacturers of latex tubing claim that the latex tubing is self-sealing, tests have indicated that leakage occurs under normal operating conditions. Another disadvantage with such sampling/injection methods is the possibility that the needle of a hypodermic needle, for example, may pass through both walls of the tubing and possibly stick and injure the clinician's skin. The risk of blood contact by the clinician would therefore exist every time a sample is withdrawn or injected into the latex tubing.

Figure 14:
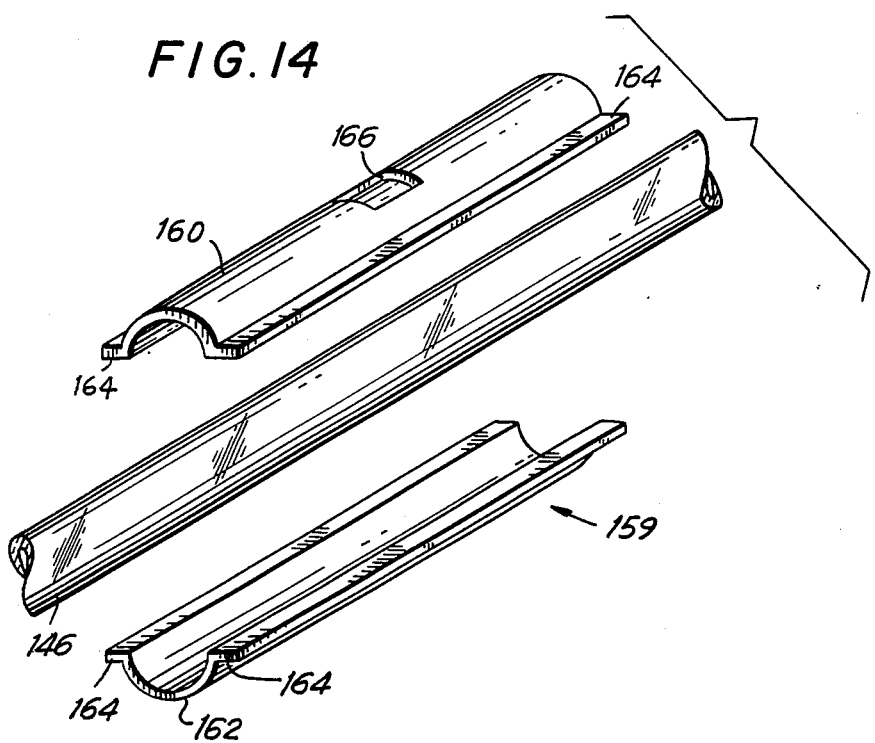
FIG. 14 is an exploded view of the injection/sampling device according to the present invention.

Therefore, the present invention also includes a device 159 for compressing tubing 146 preferably formed of latex which extends from suction inlet 36 and whose other end is adapted for insertion into the body cavity or portion which is to be drained of fluids and gases. According to the compression device 159 of the present invention as shown in FIG. 14, fresh drainage samples or infusion of drugs can be provided through the latex tubing 146 without any danger of leakage or contamination of the clinician due to possible sticks with the hypodermic. The compression device 159 of the present invention maintains at least a portion of the wall of the tubing 146 in compression and thereby provides for self-sealing of the tubing wall while additionally providing access with a hypodermic needle.

Figure 15:
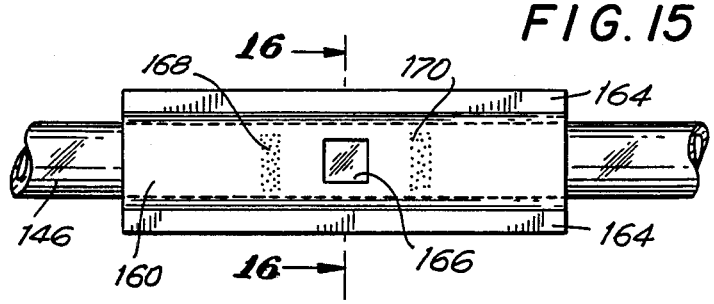
FIG. 15 is a top view of the injection/sampling device of FIG. 14.
Figure 16:
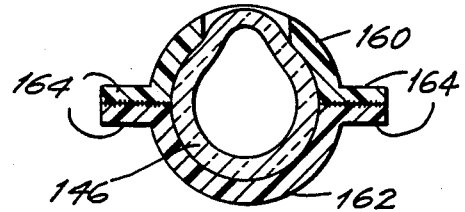
FIG. 16 is a cross-sectional side view taken along the lines 16—16 of FIG. 15 illustrating tubing under compression.

The device 159 includes a pair of compression plates—upper compression plate 160 and a lower compression plate 162—which have, when assembled, an inner cross-sectional diameter that is smaller than the cross-sectional outer diameter of the tubing 146. The plates 160 and 162 are like structured and curved as illustrated in FIG. 14. Flanges 164 along their respective longitudinal edges as shown in FIG. 14 permit securing along the respective edges of plates 160, 162 by suitable means such as gluing, welding or the like as well as other means well known to those skilled in the art. The upper plate 160 includes a central port or window 166 that allows the tubing 146 to be exposed. Since the inner cross-sectional diameter of assembled plates 160, 162 is less than the cross-sectional outer diameter of the tubing 146—preferably 20% less—the tubing 146 extends outwardly of the window 166 portion of upper plate 160 as shown more clearly in FIG. 16. In this manner, the tubing 146 at least within the portion of the window 166 is maintained under compression so that when a hypodermic needle is injected through the tubing 146 through window 166 and thereafter removed, the tubing 146 will self-seal and prevent any escape of fluid. Preferably, as shown in FIG. 15, the tubing 146 is also glued with a suitable solvent at portions 168, 170 which are adjacent the window portion 166. This permits the retention of the tubing 146 and particularly that portion about the window 166 even if the tubing is handled or pulled at portions outside of the compression device 159. Such handling of the tubing occurs when medical personnel milk the tubing 146 in the fashion as noted above in order to remove any clots for example from the drainage line. By means of the glued portions 168 and 170 the tubing is assured of being retained in its position within the device 159. At least the back plate member is relatively rigid so as to prevent a hypodermic needle from penetrating into the clinician's skin in the manner as described above.

Referring to FIG. 4 the visual indicator as noted above includes a float member 172 which is positioned in the first compartment 64 of the suction control chamber 16 and in particular in the upper portion thereof adjacent the juncture of the first compartment 64 and the large arm 46 of the seal chamber 14. The float member 172 is dimensioned and configured so as to be capable of moving within a confined region 174 which is determined between a pair of post members 176, 178 that serve as stops to limit the movement of the float member 172 within the confined region 174. The float member 172 is critically sized as is also the confined region 174 so that the float member will move upwardly within the confined region 174 when the predetermined preset level of suction as controlled by regulator 72 is obtained in the collection chamber 12. Accordingly, in such circumstance, the float member 172 will rise toward stop 176 when the proper predetermined level of suction is achieved and overcome. In order to permit viewing of the float member 172, the front wall 110 has a visible portion 150 which permits viewing of the float member 172 as it moves upwardly towards stop member 176. This provides to the medical personnel immediate visual confirmation that the chest drainage device 10 has a proper operation of suction in the collection chamber 12. Preferably, the float member 172 is colored in contrast to its surrounding so as to be readily visible. In a preferred embodiment, the float member 172 is fluorescent so as to provide immediate visual confirmation of proper suction operation even in reduced light or night conditions.

Notably, the dry or waterless suction control chamber 16 is independent of any fluid which in typical drainage devices provides the degree of suction. However, the evaporation of the fluid in those typical drainage devices results in variations in the suction pressure. This variation is avoided by means of the dry suction control chamber 16 of the present invention which is not dependent on any fluid to control or regulate suction.

Thus, the regulator 72 of the present invention does not employ water to control suction. In operation, the positioning of the setting of the suction level will be accomplished by turning the dial 104. The position of the dial 104 will cause spring 82 to be elongated accordingly. Elongation of the spring 82 causes a force to be exerted on the valve plate 76 which seats against opening 78. The exerted force is a function of the degree of spring elongation and the spring's physical properties. Once suction is appled to the collection chamber 12 and thereby the chest cavity or body portion of the patient, a force will be applied to the valve plate 76. If the force applied to the valve plate 76 resulting from the applied suction exceeds the force supplied from elongation of the spring 82, the plate valve 76 will be displaced allowing ambient or atmospheric air to enter the chest drainage device chambers. In particular, atmospheric air enters in through opening 74, through opening 78 in wall 80, around smaller sized wall 88, through opening 79 in wall 81 and thus through the second compartment 67 and through first compartment 64 of the suction control chamber 16 and up out of the suction inlet 60. The plate valve 76 will remain displaced until the point where the force balance is achieved and thereupon the plate valve 76 will once again seat and seal the opening 78. The regulation of imposed suction as described above, however, will provide rapid modulation of the plate seat 76 as those differentials occur. In order to reduce or attenuate this modulation, the dashpot 86 is included whose structure has been described hereinabove.

According to the configuration of the regulator 72 and its location in the chest drainage device 10, preferential air flow is provided which permits evacuation of air preferentially from the patient rather than from the regulator 72. This is assured by the area of opening 78 being larger than the smallest cross-sectional area of any passage in any of the chambers. Thus, the system allows variations in patient air leaks and also source suction levels while maintaining a predetermined preset imposed level of suction in the collection chamber 12. Accordingly, the chest drainage device 10 according to the present invention is insensitive to pressure variations regardless of their source and provides a generally steady level of suction in accordance with the predetermined preset level of suction as regulated by the suction control regulator 72 and as indicated by the dial 104 setting.

In comparison, typical dry chest drainage device regulator systems employ a restricted orifice located in the suction application line. These systems are ineffective in maintaining a desired imposed suction pressure level and rather restrict volume flow of air through such systems.

In an alternative embodiment of the present invention, the float member 172 can be optionally replaced by means of a bubbler indicator which will provide not only visible but also audible immediate confirmation of the proper level of suction in the collection chamber 12. The bubbler indicator includes a bubbler zone which is formed at the juncture of the lower ends of the first compartment 64 and the second compartment 67 of the suction control chamber 16. A predetermined amount of fluid is admitted into the bubbler zone so that under operational conditions, any ambient or atmospheric air entering through the regulator 72 will pass through the bubbler zone and will bubble therethrough toward the suction inlet 60 and thus provide audible confirmation of proper operation of suction in the collection chamber 12. By providing a transparent portion 148 on front wall 110 as shown in FIG. 1, visual confirmation is also provided. Thus, medical personnel upon passing the chest drainage device 10 as illustrated in FIGS. 1 and 4 will be able to both hear and see that the chest drainage device 10 is operating properly.

However, since the plate valve 76 is not a perfect seal and in most instances will permit some air or ambient to pass through toward the suction inlet 60, a critically sized passageway 180 is provided in wall member 182 separating the first compartment 64 and second compartment 67 and is positioned at a point above the level of the predetermined amount of fluid admitted into the bubbler zone. In this fashion, any leakage air will bypass the bubbler zone and travel directly into the suction line without providing a false alarm of operation which is not yet achieved since the predetermined preset level of suction is yet to be obtained. A grommet 140 as previously described is provided through which the fluid may be admitted. Alternatively, a suitably sized flexible injection tubing (not shown) can be inserted through the suction inlet 60 and positioned down to the lower portion of first compartment 64 and thereupon provide for admission of fluids. Similarly, the injection flexible tubing can also be passed into the large arm 46 of the seal chamber 14 and thereby provide for admission of fluid. In these alternative operations, there will be no need for the grommets 140 and 138 as illustrated in FIG. 1. Thus, after a predetermined amount of fluid is injected into the bubbler zone, any atmospheric air passing therethrough will cause bubbling in the suction control chamber 16 when the applied suction exceeds the preset imposed value. The bubbler zone and regulator 72 are designed so that the addition or deletion of water in the bubbler zone will have no effect whatsoever upon the imposed suction level. The bubbler zone and first compartment 64 and second compartment 67 include deflectors 182, 184 and 186 which aid in preventing any fluid in the bubbler zone from rising and spilling over into the seal chamber 14. In addition, the height of the second compartment 64 is chosen so as to further aid in preventing such spillover. Notably, the amount of predetermined fluid in the bubbler zone is below that level required to open the valve plate 76. In comparison with the float member 172, the amount of predetermined fluid corresponds to the inertial mass of float member 172.

Although the suction regulator 72 of the present invention has bee described in connection with a chest drainage device 10, it can also be applied to control suction of other drainage devices as well. As shown in FIG. 4 wall member portions 190, 192 and 194 are provided for added support.

The present invention has been described in detail with particular emphasis on the preferred embodiments thereof. However, it should be understood that variations and modifications within the spirit and scope of the invention may occur to those skilled in the art to which the invention pertains.

We claim:

1. Apparatus for draining bodily fluids comprising:
   a. collection chamber for collecting fluids from a body cavity, said collection chamber including an inlet for fluid communication with the body cavity;
   b. seal chamber for preventing passage of atmospheric air into the body cavity; and
   c. suction control chamber for meterlessly regulating the degree of vacuum imposed in the collection chamber and including:
      1. first compartment communicating at one end with said seal chamber and having an inlet for coupling to a suction source;
      2. second compartment communicating at one end with the other end of said first compartment and at its other end having an inlet for communicating with the ambient;
      3. discrete dry meterless means for regulating the degree of suction imposed in said collection chamber at a plurality of predetermined preset levels of suction such that said regulation is substantially insensitive to pressure variations due to patient air leaks or suction source levels, said regulating means positioned within said second compartment, said dry regulating means dimensioned and configured so as to provide suction control at said predetermined preset level of suction independently of any liquid within said suction control chamber; and
      4. indicator means positioned within said first compartment for providing immediate confirmation of proper operation of suction of the body cavity.

2. The apparatus according to claim 1 wherein said regulation suction means comprises:
   a. a member positioned within and dividing said second compartment into a first portion adjacent said ambient inlet and a remaining second portion, said member having an aperture for passage of ambient into said first compartment;
   b. valve means dimensioned and configured for opening and closing said aperture; and
   c. means for tensioning said valve means closed when the collection chamber suction is at said preset level of suction and otherwise opening said valve means so as to permit ambient to flow into said second portion of said second compartment and thereby return the suction in the collection chamber to said preset level.

3. The apparatus according to claim 2 further comprising means for adjusting said spring tension in predetermined preset discrete steps so as to provide one of said predetermined preset levels of suction.

4. The apparatus according to claim 2 wherein said aperture in area is greater than the smallest cross-sectional area of any passage in any of the chambers.

5. Apparatus for draining bodily fluids comprising:
   a. collection chamber for collecting fluids from a body cavity, said collection chamber including an inlet for fluid communication with the body cavity;
   b. seal chamber for preventing passage of atmospheric air into the body cavity; and
   c. suction control chamber for meterlessly regulating the degree of vacuum imposed in the collection chamber and including:
      1. first compartment communicating at one end with said seal chamber and having an inlet for coupling to a suction source;
      2. second compartment communicating at one end with the other end of said first compartment and at its other end having an inlet for communicating with the ambient;
      3. dry means for regulating the degree of suction imposed in said collection chamber at a plurality of predetermined preset levels of suction, said regulating means positioned within said second compartment; and
      4. indicator means positioned within said first compartment for providing immediate confirmation of proper operation of suction of the body cavity;

said regulation suction means comprises:
   a. a member positioned within and dividing said second compartment into a first portion adjacent said ambient inlet and a remaining second portion, said member having an aperture for passage of ambient into said first compartment;
   b. valve means dimensioned and configured for opening and closing said aperture; and
   c. means for tensioning said valve means closed when the collection chamber suction is at said preset level of suction and otherwise opening said valve means so as to permit ambient to flow into said second portion of said second compartment and thereby return the suction in the collection chamber to said preset level;

further comprising means for adjusting said tension in predetermined preset discrete steps so as to provide one of said predetermined preset levels of suction; wherein said adjusting means comprises:
   a. worm gear disposed on at least a mid portion of said support member;
   b. pinion gear being rotatably supported and cooperatively engaging said worm gear;

c. dial coupled to said pinion gear and having a plurality of predetermined preset grooves along its periphery;

d. detent member resiliently disposed against said periphery and configured and dimensioned for seating within one of said grooves and such that upon rotating said dial, said detent member rides along said periphery until seating within next one of said grooves.

6. The apparatus according to claim 5 further comprising means for variably calibrating the tension of said spring while said detent member is seated within one of said predetermined preset grooves of said dial o that said spring tension can be selectively varied without any rotation of said dial.

7. The apparatus according to claim 6 wherein said tension calibration means comprises a collar rotatably disposed in a portion of said housing, said other end of said support member being secured to said collar for rotation therewith so that upon rotation of said collar together with said support member, the tension of said spring can be selectively varied while said dial is stationary.

8. The apparatus according to claim 7 wherein at least a portion of said dial extends out of said ambient inlet so that said dial can be rotated from outside of said suction control chamber.

9. The apparatus according to claim 8 wherein said dial has graduations thereon to indicate the suction pressure imposed in said collection chamber while said detent member is seated in one of said grooves.

10. Apparatus for draining bodily fluids comprising:
a. collection chamber for collecting fluids from a body cavity, said collection chamber including an inlet for fluid communication with the body cavity;
b. seal chamber for preventing passage of atmospheric air into the body cavity; and
c. suction control chamber for meterlessly regulating the degree of vacuum imposed in the collection chamber and including:
 1. first compartment communicating at one end with said seal chamber and having an inlet for coupling to a suction source;
 2. second compartment communicating at one end with the other end of said first compartment and at its other end having an inlet for communicating with the ambient;
 3. dry means for regulating the degree of suction imposed in said collection chamber at a plurality of predetermined preset levels of suction, said regulating means positioned within said second compartment; and
 4. indicator means positioned within said first compartment for providing immediate confirmation of proper operation of suction of the body cavity;

said regulation suction means comprises:
a. a member positioned within and dividing said second compartment into a first portion adjacent said ambient inlet and a remaining second portion, said member having an aperture for passage of ambient into said first compartment;
b. valve means dimensioned and configured for opening and closing said aperture; and
c. means for tensioning said valve means closed when the collection chamber suction is at said preset level of suction and otherwise opening said valve means so as to permit ambient to flow into said second portion of said second compartment and thereby return the suction in the collection chamber to said preset level;

wherein said valve mean is a generally flat plate having a circular bead on one side thereof for seating against said separation member and about said aperture so as to provide in cross section a generally single point of contact between said bead and said separation plate.

11. Apparatus for draining bodily fluids comprising:
a. collection chamber for collecting fluids from a body cavity, said collection chamber including an inlet for fluid communication with the body cavity;
b. seal chamber for preventing passage of atmospheric air into the body cavity; and
c. suction control chamber for meterlessly regulating the degree of vacuum imposed in the collection chamber and including:
 1. first compartment communicating at one end with said seal chamber and having an inlet for coupling to a suction source;
 2. second compartment communicating at one end with the other end of said first compartment and at its other end having an inlet for communicating with the ambient;
 3. dry means for regulating the degree of suction imposed in said collection chamber at a plurality of predetermined preset levels of suction, said regulating means positioned within said second compartment; and
 4. indicator means positioned within said first compartment for providing immediate confirmation of proper operation of suction of the body cavity;

said regulation suction means comprises:
a. a member positioned within and dividing said second compartment into a first portion adjacent said ambient inlet and a remaining second portion, said member having an aperture for passage of ambient into said first compartment;
b. valve means dimensioned and configured for opening and closing said aperture; and
c. means for tensioning said valve means closed when the collection chamber suction is at said preset level of suction and otherwise opening said valve means so as to permit ambient to flow into said second portion of said second compartment and thereby return the suction in the collection chamber to said preset level;

further comprising damping means coupled to said valve means for attenuating any rapid movement of said valve means during opening and closing of said aperture in response to any suction variations from said predetermined preset level of suction.

12. The apparatus according to claim 11 wherein said damping means comprises a dashpot operatively connected to said valve means.

13. The apparatus according to claim 12 wherein said spring is disposed in said first portion adjacent said ambient inlet and said valve means and said dashpot are each disposed in said second portion of said second compartment.

14. Apparatus for draining bodily fluids comprising:
a. collection chamber for collecting fluids from a body cavity, said collection chamber including an inlet for fluid communication with the body cavity;
b. seal chamber for preventing passage of atmospheric air into the body cavity; and c. suction control chamber for meterlessly regulating the degree of vacuum imposed in the collection chamber and including:
1. first compartment communicating at one end with said seal chamber and having an inlet for coupling to a suction source;
2. second compartment communicating at one end with the other end of said first compartment and at its other end having an inlet for communicating with the ambient;
3. dry means for regulating the degree of suction imposed in said collection chamber at a plurality of predetermined preset levels of suction, said regulating means positioned within said second compartment; and
4. indicator means positioned within said first compartment for providing immediate confirmation of proper operation of suction of the body cavity; wherein said indicator means comprises a float disposed within a confined region of said first compartment of said suction chamber, said confined region having a visible portion and said float being configured and dimensioned so as to move to said visible portion within said confined portion when said predetermined preset level of suction is obtained in said collection chamber and thereby provide immediate visual confirmation of proper operation of suction in said collection chamber.

15. The apparatus according to claim 14 wherein said confined region is defined between a pair of stop members and which limit the movement of said float within said confined region.

16. The apparatus according to claim 15 wherein said float is colored in contract to its surroundings so as to be readily visible.

17. The apparatus according to claim 16 wherein said float is flourescent so as to provide immediate visual confirmation of proper suction operation in reduced light or night conditions.

18. Apparatus for draining bodily fluids comprising:
a. collection chamber for collecting fluids from a body cavity, said collection chamber including an inlet for fluid communication with the body cavity;
b. seal chamber for preventing passage of atmospheric air into the body cavity; and
c. suction control chamber for meterlessly regulating the degree of vacuum imposed in the collection chamber and including:
1. first compartment communicating at one end with said seal chamber and having an inlet for coupling to a suction source;
2. second compartment communicating at one end with the other end of said first compartment and at its other end having an inlet for communicating with the ambient;
3. dry means for regulating the degree of suction imposed in said collection chamber at a plurality of predetermined preset levels of suction, said regulating means positioned within said second compartment; and
4. indicator means positioned within said first compartment for providing immediate confirmation of proper operation of suction of the body cavity; wherein said indicator means comprises a visible bubbler zone formed at the juncture of said first and said second compartments for retaining a predetermined amount of fluid so that under operational conditions ambient entering through said bubbler zone will bubble therethrough toward said suction inlet and thus provide both immediate visual and audible confirmation of proper operation of suction in said collection chamber.

19. The apparatus according to claim 18 wherein said bubbler zone includes a passageway bypassing said fluid retention zone, said passageway being dimensioned and configured so that ambient will not bubble through fluid in said bubbler zone until said suction imposed in said collection chamber is at least above set predetermined preset level of suction.

20. Apparatus for draining bodily fluids comprising:
a. collection chamber for collecting fluids from a body cavity, said collection chamber including an inlet for fluid communication with the body cavity;
b. suction control chamber for regulating the degree of vacuum imposed in the collection chamber; and
c. seal chamber for preventing passage of ambient into the collection chamber and including:
(1) a large arm compartment having a suction inlet at one end;
(2) a small arm compartment at one end having an opening communicating with said collection chamber and communicating at its other end with the other end of said large arm, said small arm compartment having means adjacent its one end for preventing ambient form passing into said collection chamber when said collection chamber has a relatively high level of negative pressure; wherein said ambient prevention means comprises a first chamber formed adjacent said opening and being dimensioned and configured so as to contain the entire volume of a predetermined amount of sealing fluid disposed in said seal chamber at the juncture of said large arm and said small arm compartments; said containment chamber being configured so that any sealing fluid passing into said containment chamber is diverted in a direction other than the direction of normal flow so that entering fluid will circulate in and be collected within said containment chamber; and
further comprising:
a. wall member positioned within said small arm and separating said containment chamber from the remainder of said small arm, said wall member having an aperture; and
b. valve means being dimensioned and configured for opening and substantially closing said aperture, said valve means being open when the collection chamber suction is at said preset level of suction and otherwise said valve means tending to substantially close said aperture in response to any fluid entering into said containment chamber from said juncture of said large arm and said small arm compartments; wherein said valve means comprises a ball dimensioned and configured so as to be adapted for seating with and substantially closing said aperture; and wherein said aperture includes a notch so as to permit the sealing fluid to enter into said containment chamber when said ball valve seats upon and substantially closes said opening whereupon the sealing fluid is diverted within said containment chamber generally transverse to the direction normal suction flow.

21. The apparatus according to claim 20 wherein said remaining portion of said small arm is smaller in cross sectional area than that of said containment chamber.

22. The apparatus according to claim 20 wherein said remaining portion of said small arm is constricted so as to retain said ball valve movably between said constriction and said aperture.

23. Apparatus for draining bodily fluids comprising:
a. collection chamber for collecting fluids from a body cavity, said collection chamber including an inlet for fluid communication with the body cavity;
b. suction control chamber for regulating the degree of vacuum imposed in the collection chamber; and
c. seal chamber for preventing passage of ambient into the collection chamber and including:
  (1) a large arm compartment having a suction inlet at one end;
  (2) a small arm compartment at one end having an opening communicating with said collection chamber and communicating at its other end with the other end of said large arm, said small arm compartment having means adjacent its one end for preventing ambient from passing into said collection chamber when said collection chamber has a relatively high level of negative pressure; wherein said ambient prevention means comprises a one-way check valve disposed and oriented in said small arm compartment, said valve being open so as to permit the passage of suction flow from said collection chamber into said suction inlet, but being closed so as to prevent ambient from passing into said collection chamber.

24. The apparatus according to claim 21 wherein said one-way check valve is positioned adjacent said opening communicating said small arm compartment with said collection chamber.

25. Apparatus for draining bodily fluids comprising:
a. collection chamber for collecting fluids from a body cavity, said collection chamber including an inlet for fluid communication with the body cavity;
b. suction control chamber for regulating the degree of vacuum imposed in the collection chamber; and
c. seal chamber for preventing passage of ambient into the collection chamber and including:
  (1) a large arm compartment having a suction inlet at one end;
  (2) a small arm compartment at one end having an opening communicating with said collection chamber and communicating at its other end with the other end of said large arm, said small arm compartment having means adjacent its one end for preventing ambient from passing into said collection chamber when said collection chamber has a relatively high level of negative pressure;
further comprising an air flow meter disposed at the juncture of the other ends of said small arm and large arm, said air flow meter providing for measurement of the quantity of gases passing from the body cavity.

26. Chest drainage device for draining fluids from a body cavity or portion comprising:
a. housing;
b. collection chamber formed within said housing for collecting fluids including an inlet for entry of the fluids and for fluid communication with the body cavity or portion;
c. seal chamber formed within said housing for preventing passage of ambient into the collection chamber and including:
  (1) a large arm compartment having a suction inlet at one end for coupling to a suction source;
  (2) a small arm compartment at one end having an opening communicating with said collection chamber and communicating at its other end with the other end of said large arm, said small arm compartment having means adjacent its one end for preventing ambient from passing into said collection chamber when said collection chamber has a relatively high level of negative pressure;
d. suction control chamber formed within said housing and being in fluid communication with said collection chamber for meterlessly regulating the degree of vacuum imposed in the collection chamber and pleural cavity and including:
  (1) first inlet for coupling to said suction inlet of said seal chamber;
  (2) second inlet communicating with the ambient;
  (3) discrete dry meterless means for regulating the degree of suction imposed in said collection chamber at a plurality of predetermined preset levels of suction, said regulating means disposed between said first inlet and said ambient inlet, said dry regulating means dimensioned and configured so as to provide suction control at said predetermined preset level of suction independently of any liquid within said suction control chamber; and
  (4) indicator means disposed between said regulating means and said first inlet for providing immediate confirmation of proper operation of suction in said collection chamber.

27. The apparatus according to claim 26 wherein said housing is formed of a front wall member and a back wall member sealed together along their peripheries by a plurality of side wall members.

28. The apparatus according to claim 27 wherein said front wall member includes an integrally formed handle.

29. The apparatus according to claim 28 wherein said suction inlet and collection chamber inlet are each disposed in a first side wall common to said seal chamber and said collection chamber.

30. The apparatus according to claim 29 wherein said ambient inlet to said suction control chamber is disposed in a second side wall adjacent to said first side wall.

31. The apparatus according to claim 30 further comprising an elongated support stand rotatably secured to a third side wall opposite said first side wall so that said support stand can be rotated from a stored position to a support position wherein said support stand is generally transverse to said third side wall so as to stably support said housing at a predetermined location.

32. The application according to claim 31 further comprising means for securing said support stand in said support position.

33. The apparatus according to claim 32 wherein at least portions of said housing are transparent to permit viewing of the operation or contents of underlying portions of each of said collection, seal and suction control chambers.

34. The apparatus according to claim 33 wherein at least selected portions of said front wall member are marked with graduations so as to identify the volume of the contents thereof and with predetermined indicia to provide instructional information.

* * * * *